United States Patent
Sankai (10) Patent No.: US 11,344,229 B2
(45) Date of Patent: May 31, 2022

(54) WEARABLE GAIT DETECTION DEVICE, WALKING ABILITY IMPROVEMENT SYSTEM AND WEARABLE GAIT DETECTION SYSTEM

(71) Applicants: CYBERDYNE INC., Tsukuba (JP); UNIVERSITY OF TSUKUBA, Tsukuba (JP)

(72) Inventor: Yoshiyuki Sankai, Ibaraki (JP)

(73) Assignees: CYBERDYNE INC., Tsukuba (JP); UNIVERSITY OF TSUKUBA, Tsukuba (JP)

( * ) Notice: Subject to any disclaimer, the term of this patent is extended or adjusted under 35 U.S.C. 154(b) by 473 days.

(21) Appl. No.: 15/999,426

(22) PCT Filed: Feb. 17, 2017

(86) PCT No.: PCT/JP2017/005993
§ 371 (c)(1),
(2) Date: Mar. 12, 2019

(87) PCT Pub. No.: WO2017/142082
PCT Pub. Date: Aug. 24, 2017

(65) Prior Publication Data
US 2021/0204836 A1    Jul. 8, 2021

(30) Foreign Application Priority Data
Feb. 19, 2016 (JP) .............................. JP2016-030374

(51) Int. Cl.
*A61B 5/11* (2006.01)
*A61B 5/00* (2006.01)
*A61B 5/103* (2006.01)

(52) U.S. Cl.
CPC ............ *A61B 5/112* (2013.01); *A61B 5/0004* (2013.01); *A61B 5/0022* (2013.01);
(Continued)

(58) Field of Classification Search
CPC ..... A61B 5/112; A61B 5/1038; A61B 5/6807; A61B 5/0004; A61B 5/0022;
(Continued)

(56) References Cited

U.S. PATENT DOCUMENTS

2007/0073196 A1    3/2007  Tanaka et al.
2009/0273311 A1 *  11/2009 Beers ...................... H02J 50/40
                                              320/108
(Continued)

FOREIGN PATENT DOCUMENTS

GB           2527168 A  * 12/2015  ........... A61H 1/0262
JP       2009-125506 A      6/2009
(Continued)

OTHER PUBLICATIONS

Bae et al. "A Mobile Gait Monitoring System for Abnormal Gait Diagnosis and Rehabilitation: A Pilot Study for Parkinson Disease Patients", Apr. 2011, Journal of Biomechanical Engineering (Year: 2011).*
(Continued)

*Primary Examiner* — Devin B Henson
(74) *Attorney, Agent, or Firm* — Procopio, Cory, Hargreaves & Savitch LLP (57) ABSTRACT

A wearable gait detection device, a walking ability improvement system and a wearable gait detection system detect manifestation in a brain based on the wearer's gait and preventive measures. A load measurement part measures a load of a sole of the wearer's feet, a foot movement detection part at the shoes detects acceleration and/or angular velocity during feet movement, a centroid position calculation part calculates a centroid position of the feet based on changes in measured load, a movement locus calculation part calculates a movement locus of the feet based on acceleration and/or angular velocity detected by the foot movement detection part, a manifestation recognition part recognizes manifestation in the brain according to a specificity of centroid fluctuation of the feet based on the calculated centroid position and movement locus of the feet, and a sensory output part feeds back a sensation to the wearer based on a recognition result.

7 Claims, 5 Drawing Sheets

(52) U.S. Cl.
CPC .......... *A61B 5/1038* (2013.01); *A61B 5/4082* (2013.01); *A61B 5/4088* (2013.01); *A61B 5/6807* (2013.01); *A61B 2560/0214* (2013.01); *A61B 2562/0219* (2013.01)

(58) Field of Classification Search
CPC ................ A61B 5/4082; A61B 5/4088; A61B 2562/0214; A61B 2562/0219
See application file for complete search history.

(56) References Cited

U.S. PATENT DOCUMENTS

| | | | |
|---|---|---|---|
| 2012/0209149 A1 | 8/2012 | Yoneyama et al. | |
| 2015/0157274 A1* | 6/2015 | Ghassemzadeh | A61B 5/7275 600/595 |

FOREIGN PATENT DOCUMENTS

| | | |
|---|---|---|
| JP | 2011-217884 A | 11/2011 |
| JP | 4911259 B2 | 1/2012 |
| JP | 2013-183809 A | 9/2013 |
| WO | 2004/103244 A1 | 12/2004 |

OTHER PUBLICATIONS

Maculewicz, J. et al., A Technology Review of the instrumented Footwear for Rehabilitation a Focus on Parkinson's Disease Patients, Frontiers in Neurology, 7, section 4, XP55613498, Jan. 20, 2016, 8 pgs.
Extended European Search Report for related EP App No. 17753336.1 dated Sep. 18, 2019, 9 pgs.
International Search Report and Written Opinion for related International Application No. PCT/JP2017/005993, dated May 16, 2017; English translation of ISR provided; 6 pages.

* cited by examiner

WEARABLE GAIT DETECTION DEVICE, WALKING ABILITY IMPROVEMENT SYSTEM AND WEARABLE GAIT DETECTION SYSTEM

CROSS-REFERENCE TO RELATED APPLICATIONS

This application is a U.S. National Stage entry of PCT Application No: PCT/JP2017/005993, filed Feb. 17, 2017, which claims priority to Japanese Patent Application No. 2016-030374, filed Feb. 19, 2016, the contents of which are incorporated herein by reference.

TECHNICAL FIELD

The present invention relates to a wearable gait detection device, a walking ability improvement system and a wearable gait detection system for preventing dementia and cerebellar dysfunction based on the wearer's daily walking state.

BACKGROUND ART

In recent years, the number of people who suffer from dementia is of an increasing trend, and, according to the announcement made by the Ministry of Health, Labour and Welfare, the number of elderly people aged 65 years or older is estimated to be approximately 4,620,000 people nationwide as of 2012, and this number is estimated to exceed 7,000,000 people in 2025.

As a method of discovering the symptom of dementia at an early stage before such symptom is discovered by others, proposed is a method of evaluating changes in the medical condition of Parkinson's disease or the like based on the cycle of repeated rhythmic movement of walking (refer to PTL 1).

Moreover, proposed is an information processing method of providing an acceleration sensor and a floor reaction sensor to the sole of the subject's feet, estimating the muscle balance of the feet based on the acceleration of the feet and the sole reaction force, and generating information for gait improvement based on the estimated muscle balance (refer to PTL 2).

Furthermore, proposed is a gait evaluation system of providing a sole force sensor to the subject's shoes, estimating the lesioned area such as a neurological disorder at the sole of the foot based on the combination of the centroid position of the subject's foot while walking and the area of the sole of the foot, and notifying a message relating to such lesion (refer to PTL 3).

CITATION LIST

Patent Literature

[PTL 1] Japanese Patent Registration No. 4911259
[PTL 2] Japanese Unexamined Patent Publication Application No. 2009-125506
[PTL 3] Japanese Unexamined Patent Publication Application No. 2013-183809

SUMMARY OF THE INVENTION

Problems to be Solved by the Invention

Nevertheless, as with PTL 1 to PTL 3 described above, while there may be cases of detecting the severity of various diseases or changes in the medical condition based on the subject's gait while the subject, who is wearing shoes equipped with a sensor, engages in daily ambulation activity, these methods merely detect an abnormality in the walking state, and were insufficient as methods for promptly discovering the manifestation of dementia or cerebellar dysfunction in the brain.

Furthermore, even if manifestation in the brain can be detected promptly, a method of deciphering the sign thereof and feeding back such information to the subject in a timely manner so as to suppress the progress of the symptom or promote the recovery from the symptom is not described anywhere in PTL 1 to PTL 3.

The present invention was devised in view of the foregoing points, and an object of this invention is to propose a wearable gait detection device, a walking ability improvement system and a wearable gait detection system capable of promptly detecting the manifestation in the brain while the wearer is walking and transmitting a sensation to the wearer.

Means to Solve the Problems

In order to achieve the foregoing object, the present invention provides a wearable gait detection device which detects a gait in a state where a wearer is wearing a pair of left and right shoes, comprising: a load measurement part which is mounted on an inner bottom part of each of the shoes and which measures a load of a sole of the wearer's feet; a foot movement detection part which is installed at a predetermined position of each of the shoes and which detects acceleration and/or angular velocity during movement of the feet; a centroid position calculation part which calculates a centroid position of each of the feet based on changes in each load measured by the load measurement part; a movement locus calculation part which calculates a movement locus of each of the feet based on each acceleration and/or each angular velocity detected by the foot movement detection part; a manifestation recognition part which recognizes manifestation in a brain according to a specificity of centroid fluctuation of each of the feet based on the calculated centroid position and movement locus of each of the feet; and a sensory output part which feeds back a sensation to the wearer based on a recognition result of the manifestation recognition part.

Consequently, the wearer can promptly recognize a gait disorder caused by manifestation in one's brain based on the sensory feedback through the sensory output part.

Moreover, with the present invention, in a case where the manifestation recognition part has recognized a predetermined manifestation, the sensory stimulation generation part sets a level and a transmission pattern of the sensation to be transmitted to the wearer according to a level of specificity of the centroid fluctuation of each of the feet.

Consequently, because an extremely strong sensory feedback is transmitted when the wearer's level of gait disorder is high, it is possible to reduce the possibility of the wearer falling due to dementia or cerebellar dysfunction.

Furthermore, the present invention further comprises an object detection part which is mounted at a front end of each of the shoes and which detects an obstacle in front of the wearer's feet while the wearer is walking, wherein the sensory stimulation generation part feeds back the sensation to the wearer based on a detection result of the object detection part only when the manifestation recognition part has recognized a predetermined manifestation.

Consequently, because the probability of the wearer unconsciously tripping over an obstacle in front of one's feet and falling down can be reduced, it is possible to prevent the wearer from falling.

The present invention additionally provides a walking ability improvement system, comprising: the foregoing wearable gait detection device; a sending part which is provided to the wearable gait detection device and which sends data representing the centroid fluctuation of each of the feet based on the manifestation recognition part; a receiving part which is provided separately from the wearable gait detection device and which receives the data sent from the sending part; and a data terminal device which sends the data received via the receiving part to a management server via a communication line.

Consequently, data of the wearer's gait status can be accumulated as the locus of the center of gravity (center of floor reaction) of each foot over a long period, and, when it is determined that there is manifestation in the brain based on the centroid fluctuation while the wearer is walking, it is possible to warn the wearer while he/she is walking by promptly notifying such manifestation to the wearer.

Furthermore, with the present invention, the sensory stimulation generation part is provided to the pair of shoes and/or the data terminal device.

Consequently, not only will the wearer be able to receive the feedback of sensation through the shoes, the wearer will also be able to receive the feedback representing a gait disorder from the sensation given by one's portable data terminal device.

Furthermore, with the present invention, the manifestation recognition part senses progression of manifestation in the wearer's brain based on the data read from the management server via the data terminal device, and the sensory stimulation generation part sets the level and transmission pattern of the sensation to be transmitted to the wearer according to the progression of manifestation obtained from the manifestation recognition part.

Consequently, it is possible to promptly assess the progression of manifestation in the brain based on one's accumulated data over a long period, and the wearer will be able to recognize such manifestation by receiving a sensory feedback according to the progression.

The present invention additionally provides a wearable gait detection system, comprising: the foregoing wearable gait detection device; a power feeding device which is provided separately from the wearable gait detection device and which is capable of feeding power, which is fed from a power source, from a predetermined power feeding system in a non-contact manner; and a power receiving device which is built into each of a pair of shoes of the wearable gait detection device, and which receives power fed from the power feeding device based on the power feeding system, and feeds the received power to a rechargeable battery for feeding operating power to an overall circuit in each of the shoes.

Consequently, the battery of the shoes of the wearable gait detection device can be automatically recharged merely be placing the shoes on the power feeding device. Accordingly, by placing the power feeding device at the front porch or shoe box of the wearer's home, the wearer can recharge the shoes without any sense of discomfort during one's daily life.

Advantageous Effects of the Invention

According to the present invention, it is possible to realize a wearable gait detection device, a walking ability improvement system and a wearable gait detection system capable of promptly detecting manifestation in a brain based on the wearer's gait and taking preventive measures.

DESCRIPTION OF EMBODIMENTS

An embodiment of the present invention is now explained with reference to the appended drawings.

[Overall Configuration of Walking Ability Improvement System]

Figure 1:
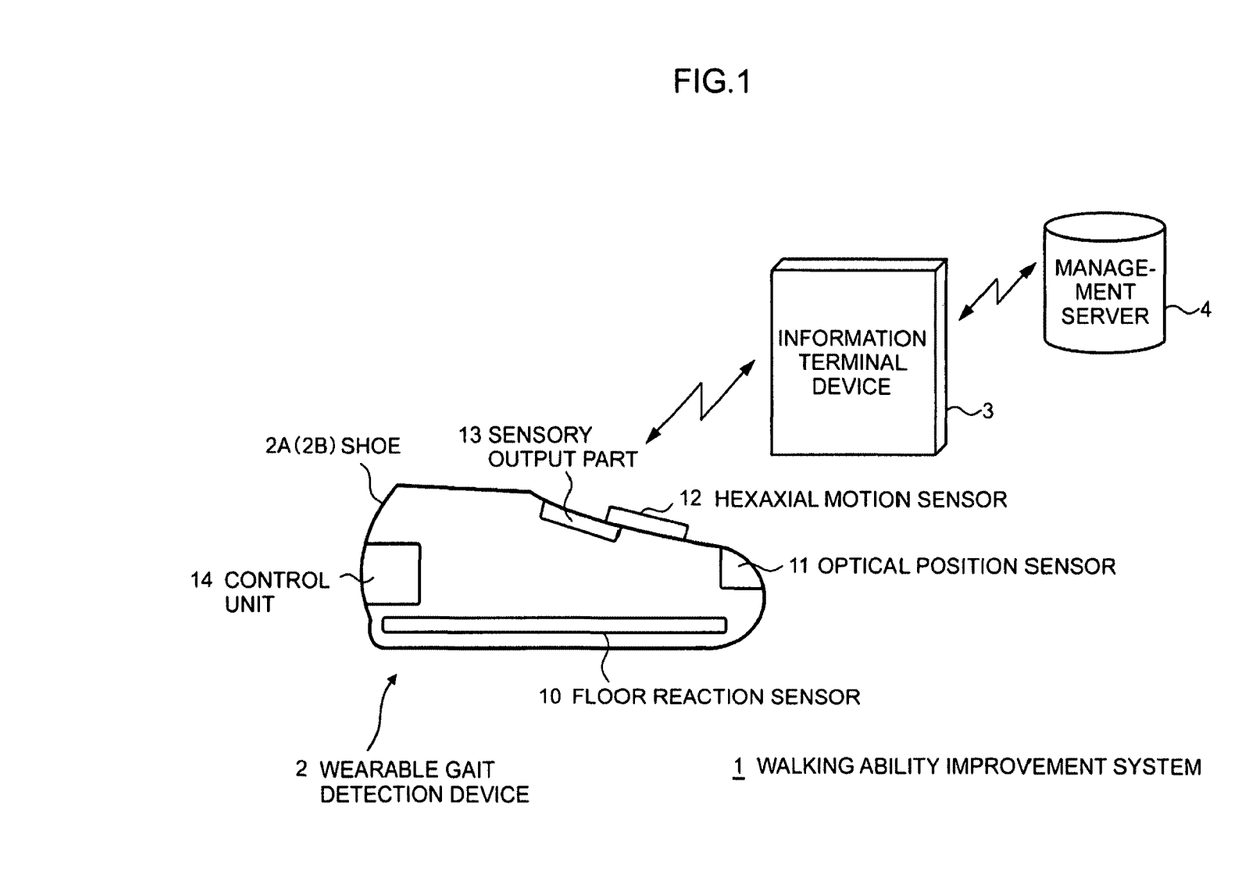
FIG. 1 is a schematic configuration diagram of the walking ability improvement system according to this embodiment.
Figure 2:
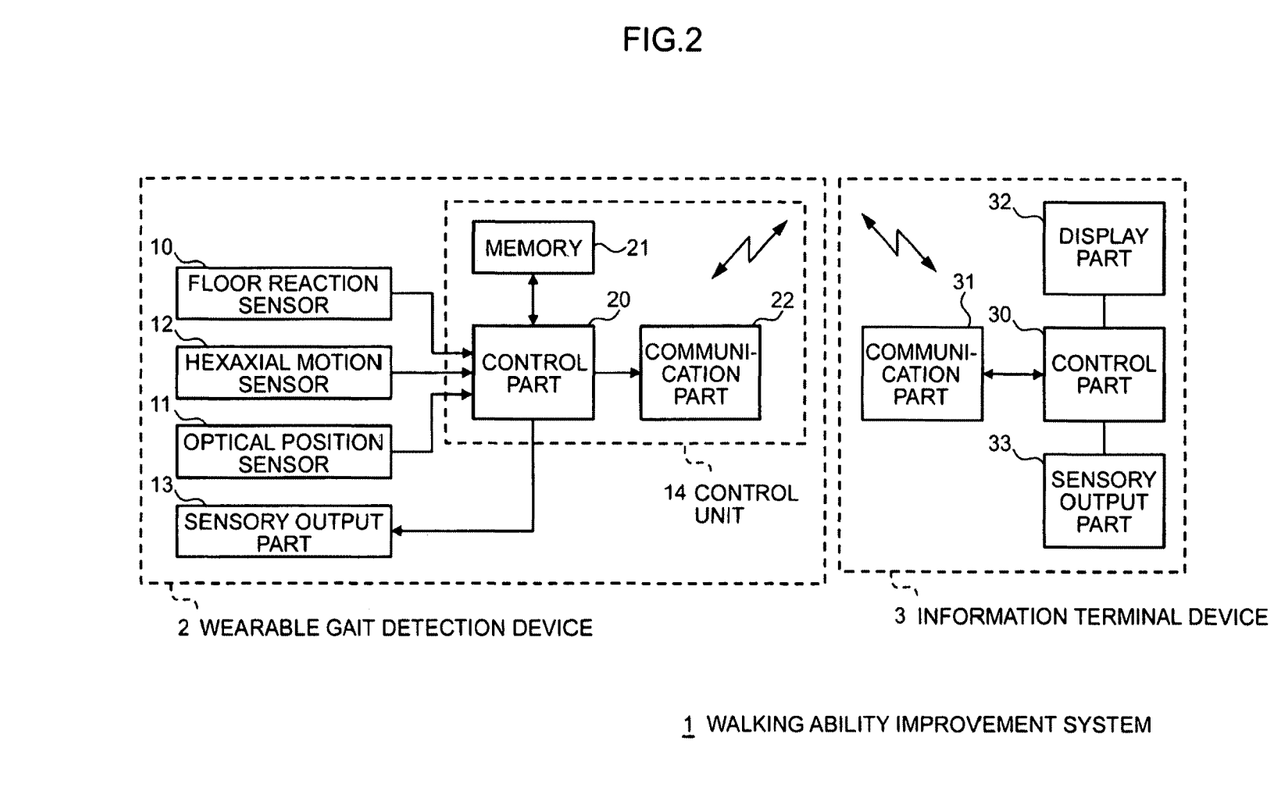
FIG. 2 is an overall configuration diagram of the walking ability improvement system according to this embodiment.

FIG. 1 and FIG. 2 show a walking ability improvement system 1 according to an embodiment of the present invention which comprises a wearable gait detection device 2 configured from a pair of shoes 2A, 2B equipped with a various sensor group, and an information terminal device 3 capable of communicating with a management server 4 connected to an external network through a wireless communication line, and is thereby able to detect the gait status of a wearer wearing the pair of shoes 2A, 2B.

Each shoe 2A (2B) of the wearable gait detection device 2 is bedded with a floor reaction sensor 10 in the sole of the shoe, and equipped with an optical position sensor 11 configured from a PSD (Position Sensitive Detector) at the front end thereof. Moreover, a hexaxial motion sensor 12 configured from a triaxial acceleration sensor and a triaxial angular velocity sensor (gyro sensor) is mounted at the upper center part of each shoe 2A (2B).

Moreover, a sensory output part 13 equipped with an LED light source, a speaker and a vibrator (vibration motor) is mounted at a part corresponding to the top of the foot in each shoe 2A (2B).

A control unit 14 configured from a control part 20, a memory 21 and a communication part 22 is mounted at the back end of each shoe 2A (2B), and the detection results from the foregoing floor reaction sensor 10, hexaxial motion sensor 12 and optical position sensor 11 are input into the control unit 14, and the control unit 14 also outputs predetermined signals to the sensory output part 13.

Accordingly, when a wearer wearing the pair of shoes 2A, 2B manifests symptoms in the brain such as dementia or cerebellar dysfunction while walking, abnormality in the gait status is estimated based on various sensor results, and sensation is fed back to the wearer in the form of light, sound, vibration or the like as needed.

Moreover, the information terminal device 3 receives, via the communication part 31, data of various sensor groups 10 and 11 that are sent wirelessly from the communication part 22 of the control unit 14 in the wearable gait detection device 2, and the control part 30 displays the related information on the display part 32, and sends the related information to an external management server 4 on the network via the communication part 31 and a wireless communication line. Here, the communication part 22 of the wearable gait detection device 2 and the communication part 31 of the information terminal device 3 are connected via a close range wireless communication system such as Bluetooth (registered trademark) or RF-ID, and data is sent and received therebetween.

The management server 4 stores data of various sensor outputs related to the wearer's gait status of each foot, and, each time the wearer wears the pair of shoes 2A, 2B of the wearable gait detection device 2 and walks, data is read via the information terminal device 3 and sent to the control unit 14 so as to enable assessment of the progression of manifestation in the brain.

Note that, similar to the wearable gait detection device 2, the information terminal device 3 also includes a sensory output part 33 equipped with an LED light source, a speaker and a vibrator (vibration motor), and is able to transmit sensory feedback to the wearer in substitute for, or together with, the wearable gait detection device 2.

[Internal Configuration of Wearable Gait Detection Device]

Figure 3:
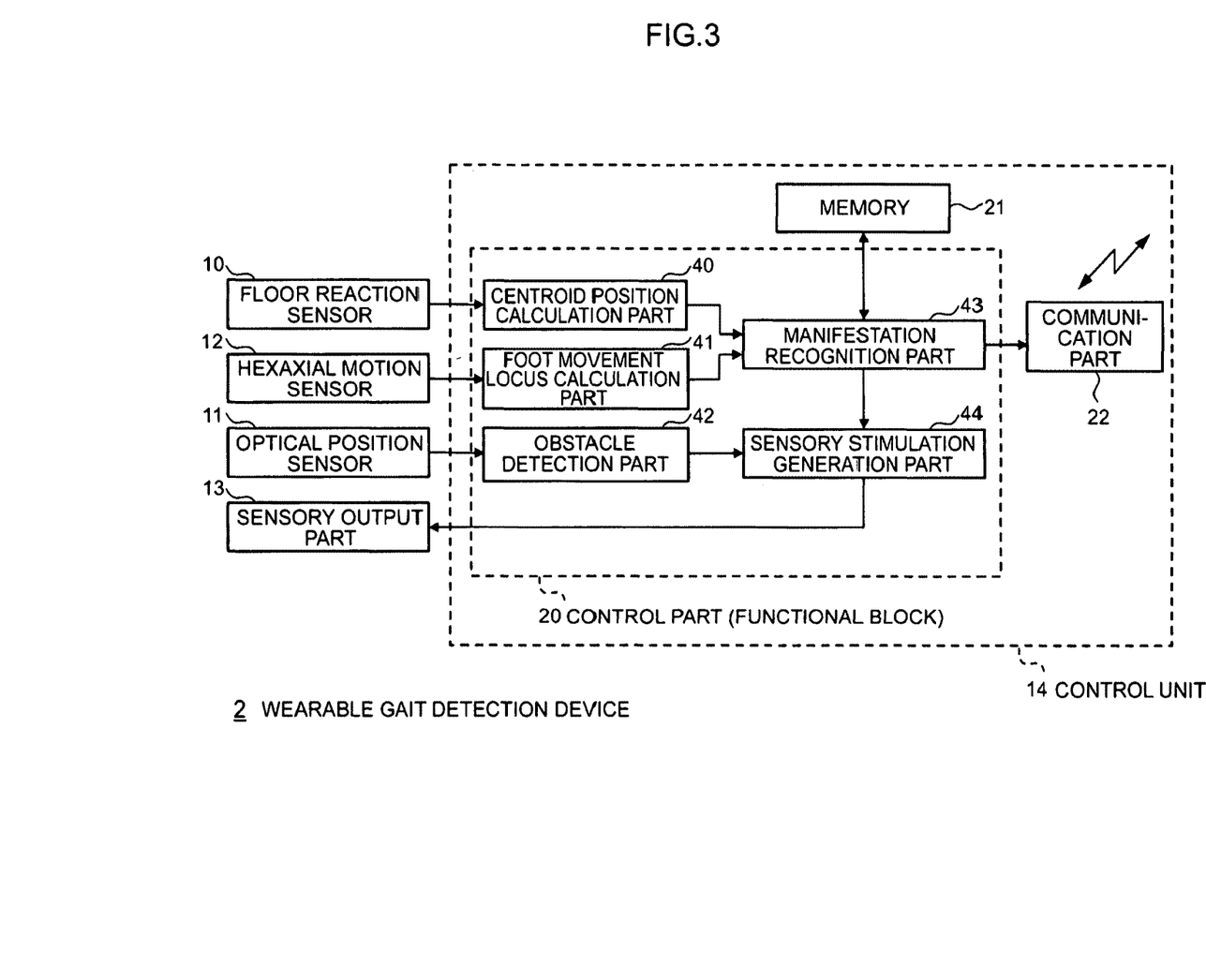
FIG. 3 is an internal configuration diagram of the wearable gait detection device according to this embodiment.

FIG. 3 is a configuration diagram of the control part 20 in the control unit 14 installed in the wearable gait detection device 2. The control part 20 is mainly configured from a micro computer, and includes the functional blocks of a centroid position calculation part 40, a foot movement locus calculation part 41, an obstacle detection part 42, a manifestation recognition part 43, and a sensory stimulation generation part 44.

The centroid position calculation part 40 receives the measurement result of the load of the sole of each foot detected by the floor reaction sensor 10, and calculates the centroid position of each foot (center of floor reaction position) based on the change of each load. As the configuration of the centroid position calculation part 40, it is desirable to adopt the same configuration as the centroid position detection device disclosed in Japanese Patent No. 4997614 in which the patentee is the same as the present applicant.

The foot movement locus calculation part 41 receives the acceleration and angular velocity during the movement of each foot detected by the triaxial acceleration sensor and the triaxial angular velocity sensor which configure the hexaxial motion sensor 12, and calculates the movement locus of each foot.

The manifestation recognition part 43 calculates the centroid fluctuation of each foot as the locus of the center of gravity (center of floor reaction) based on the centroid position of each foot calculated by the centroid position calculation part 40, and the movement locus of each foot calculated by the foot movement locus calculation part 41.

The memory 21 stores data representing the locus of the center of gravity (center of floor reaction) of each foot when the wearer is walking normally, and can be represented as a Lissajous diagram (diagram which expresses an oscillatory waveform of the gait cycle part as a closed curve on an XY plane).

Figure 4A:
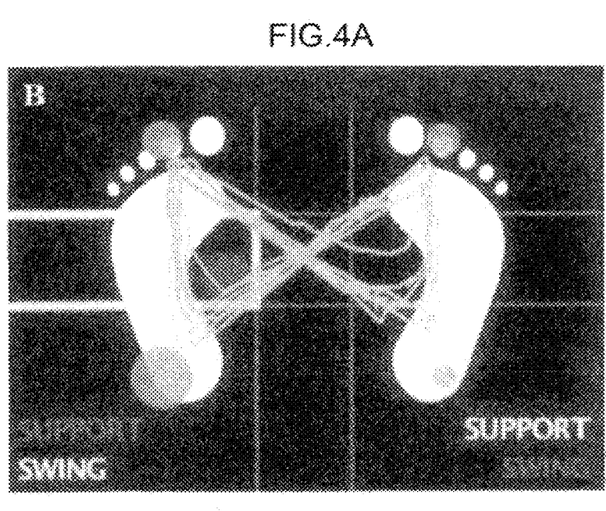
FIG. 4A is a diagram representing the Lissajous diagram reflecting the locus of the center of gravity (center of floor reaction).

As shown in FIG. 4A, with the Lissajous diagram in a normal state, the locus of the center of gravity of each foot draws a regular cycle, and is substantially constant. This is because each foot repeats the same movement during the walk, and the shift in center of gravity becomes constant.

Figure 4B:
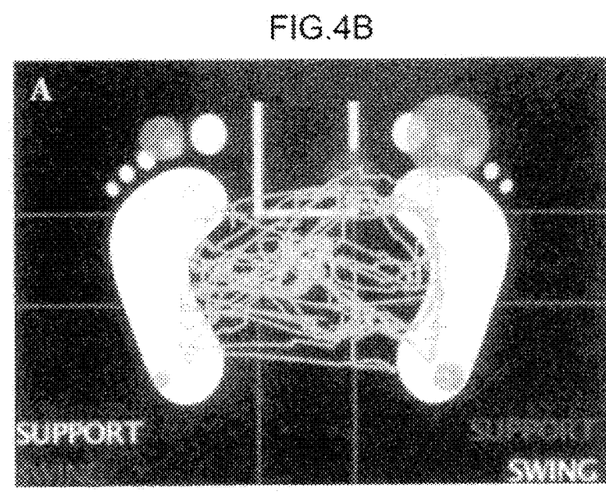
FIG. 4B is a diagram representing the Lissajous diagram reflecting the locus of the center of gravity (center of floor reaction).

Meanwhile, as shown in FIG. 4B, in a state where the wearer manifests a functional disorder in the brain such as dementia, centroid fluctuation of each foot will occur, the locus of the center of gravity becomes an irregular cycle, and the left and right balance becomes uneven. This is because the gait becomes disturbed, despite the wearer's self-consciousness, caused by the manifestation in the brain such as dementia.

The manifestation recognition part 43 reads the data representing the locus of the center of gravity of the wearer in a normal state, which is stored in the memory 21, compares it with the current locus of the center of gravity of each foot of the wearer, and evaluates the type of manifestation in the brain (dementia or cerebellar dysfunction) and the progression thereof based on the comparative result (specificity).

When the human brain actually suffers various disorders, because this will result in abnormal posture or deterioration in muscle tone, deterioration in movement velocity, and increased influence on emotional function and balance function, it is desirable to promptly perceive the change in gait before the gait disorder is revealed through external observation.

For example, with dementia, idiopathic normal pressure hydrocephalus that is often found in elderly people is a disease in which the symptom could be improved through treatment, and is a gait disorder in which the symptom could be revealed at an early stage. This gait disorder results in a state where the walker's feet are spread somewhat widely and the stride length is narrow, which leads to sliding feet, and the walker tends to lose balance when changing direction and then fall.

Generally speaking, as the types of gait disorder, in addition to dementia, there are spastic hemiplegic gait (compass gait), spastic paraplegia gait (scissors gait), Parkinson gait (tiny step gait), ataxic gait, steppage gait, waddling gait (duck gait), and intermittent claudication. The type of disorder can be generally identified based on the characteristic walking states of the foregoing gait disorders.

Among the above, the gaits which are likely caused by a disorder in the brain are spastic hemiplegic gait (compass gait), spastic paraplegia gait (scissors gait), Parkinson gait (tiny step gait), and ataxic gait.

A "spastic hemiplegic gait (compass gait)" is characterized in that the joint on the paralyzed side does not move sufficiently, the lower limb becomes stretched, and the toes sag due to a failure of the extrapyramidal tract and the upper motor neuron. Corresponding disorders are cerebrovascular disorder, mulfront endle sclerosis caused by demyelinating plaque, and cervical spondylotic myelopathy.

A "spastic paraplegia gait (scissors gait)" is characterized in that the feet are curved somewhat inward in a crouching state, and the person walks while his/her feet and knees intersect or bump into each other due to extrapyramidal disturbance on either side of both cerebral hemispheres or brainstem/lateral funiculus. Corresponding disorders are familial spastic paraplegia, cerebral palsy, and HTLV-1-associated myelopathy (HAM).

A "Parkinson gait (tiny step gait)" is characterized in that the walker engages in a unique short-stepped gait in a crouch without much waiving of the hands, and induces festination and pulsion when the symptom advances due to extrapyramidal disturbance. Corresponding disorders are Parkinson's disease and its syndromes.

A cerebellar drunken gait as one type of "ataxic gait" is characterized in that both feet are spread and cause the entire body to tremble as though the walker is drunk due to a failure of the cerebellum or vestibular nerve. Corresponding disorders are spinocerebellar degeneration (olivo-ponto-cerebellar atrophy, cerebral cortical atrophy, hereditary spinocerebellar degeneration), Wernicke's encephalopathy, vestibular neuronitis.

The characteristics of these gait disorders can be associated as the specificity of the centroid fluctuation of each foot, and these features, together the relation between the features and the symptom, are stored in the memory 21 in advance.

In other words, the characteristics of the gait disorder are stored in the memory 21 by expressing the closed curve of a two-dimensional coordinate system in which the locus of the center of gravity (center of floor reaction) of each foot is used as the oscillatory waveform of a gait cycle part (Lissajous diagram), and associating the curve data of the two-dimensional coordinate system with each gait disorder.

The memory 21 stores data representing the closed curve of a two-dimensional coordinate system in which the locus of the center of gravity (center of floor reaction) of each foot is used as the oscillatory waveform of a gait cycle part (Lissajous diagram) even when the wearer is walking normally.

The manifestation recognition part 43 calculates the waveform pattern representing the closed curve data of the two-dimensional coordinate system regarding the calculated locus of the center of gravity (center of floor reaction) in each foot of the wearer, and the manifestation recognition part 43 thereafter reads and compares the waveform pattern representing the curve data in a normal state.

Subsequently, the manifestation recognition part 43 determines with which feature of which gait disorder the difference in the waveform pattern as the comparative result is closest based on the waveform pattern (curve data) for each gait disorder stored in the memory 21, and determines the level of difference in the foregoing waveform pattern (that is, level of specificity of the centroid fluctuation of each foot) as the level of gait disorder.

The manifestation recognition part 43 outputs signals of the corresponding manifestation and progression to the sensory stimulation generation part 44 only when the determination result recognizes that it is caused by manifestation in the brain.

When the sensory stimulation generation part 44 receives an output signal from the manifestation recognition part 43, the sensory stimulation generation part 44 sets the level and transmission pattern of the sensation to be transmitted to the wearer according to the type of manifestation in the wearer's brain (type of gait disorder) and the progression thereof, and thereafter sends the signals of the setting to the sensory output part.

The sensory output part 13 transmits, in a sensory manner, any one or a combination of light, sound and vibration to the wearer by driving at least one or more among the LED device, the speaker and the vibrator at a predetermined level and output pattern based on the setting signal obtained from the sensory stimulation generation part 44.

Moreover, when the optical position sensor 11 detects an obstacle (for instance, height of the obstacle is 5 cm or higher from the ground) in a range of 10 to 80 cm in front of the wearer while walking, the obstacle detection part 42 sends the detection result to the sensory stimulation generation part 44. The sensory stimulation generation part 44 sends a predetermined warning signal to the sensory output part 13 only when the manifestation recognition part 43 recognizes a predetermined manifestation. The sensory output part 13 transmits, in a sensory manner, any one or a combination of light, sound, vibration and electrical stimulation to the wearer in a predetermined pattern based on the warning signal.

Operation According to this Embodiment

Based on the foregoing configuration, in the walking ability improvement system 1, the control part 20 of the wearable gait detection device 2 detects the centroid position and movement locus of each foot while the wearer, who is wearing the pair of shoes 2A, 2B, is walking, and calculates the locus of the center of gravity (center of floor reaction) of each foot.

Subsequently, the control part 20 compares the waveform pattern representing the locus of the center of gravity (center of floor reaction) of each foot with a normal waveform pattern of the centroid fluctuation (center of floor reaction) of each foot which is stored in advance, and determines which characteristic of the gait order caused by the manifestation in the brain is the closest based on the comparative result. Subsequently, the control part 20 controls the output method of the sensory output part 13 (one or a combination of light, sound, and vibration) according to the progression of the gait disorder.

Consequently, the wearer can promptly recognize the gait disorder caused by the manifestation in one's brain based on the sensory feedback through the sensory output part 13.

Modified Examples

In the present invention, with the wearable gait detection device 2, while a case was explained where the control unit 14 and the various sensor groups 10 to 13 are mounted at predetermined positions of the pair of shoes 2A, 2B as shown in FIG. 1, the present invention is not limited thereto, and, other than the floor reaction sensor 10 and the optical position sensor 11, the components may be freely mounted at the wearer's intended position in the shoes 2A (2B). The floor reaction sensor 10 may also be mounted freely as the inner sole of the shoes, and the wearer may select whether or not to mount the optical position sensor 11 in a detachable manner.

Moreover, in the wearable gait detection device 2 of the present invention, while a case was explained where the sensory output part 13 is configured from an LED light source, a speaker and a vibrator (vibration motor), the present invention is not limited thereto, and electrical stimulation may also be applied using a stimulation sensor in substitute for the vibrator.

Moreover, while a case of applying the motion sensor (foot movement detection part) 12 configured from a triaxial acceleration sensor and a triaxial angular velocity sensor was explained, the present invention is not limited thereto, and, so as long as it is possible to calculate the movement locus of each foot, it is possible to measure only one of either the acceleration or the angular velocity upon movement of the feet.

Furthermore, while a case of applying the optical position sensor (object detection part) 11 configured from a PSD was explained, the present invention is not limited thereto, and so as long as it is possible to detect an obstacle in front of the wearer's feet while the wearer is walking, various sensors such as an ultracompact RGB camera or a laser range sensor may also be applied.

Furthermore, in the walking ability improvement system 1 of the present invention, while the sensory feedback to the wearer was transmitted through the sensory output part 13 mounted on the pair of shoes 2A, 2B, without limitation thereto, or in addition thereto, the sensory feedback may be transmitted to the user from the sensory output part 33 of the information terminal device 3. The probability of recognition will increase when sound, light, vibration or the like is given directly from the portable information terminal device 3 in addition to being given to the wearer from the top of each foot.

Furthermore, the wearable gait detection device 2 of the present invention may be built in with a rechargeable battery (secondary battery) to build a power feeding system capable of feeding power in a non-contact (wireless) manner. As the power feeding system, considered may be an electromagnetic induction system with built-in coils, a magnetic resonance system, or an electric field resonance system with built-in electrodes.

In this embodiment, a non-contact power feeding system based on a magnetic resonance transmission system is adopted, and the positioning during the power feeding (positioning between feeding/receiving coils) is performed relatively rough.

Figure 5A:
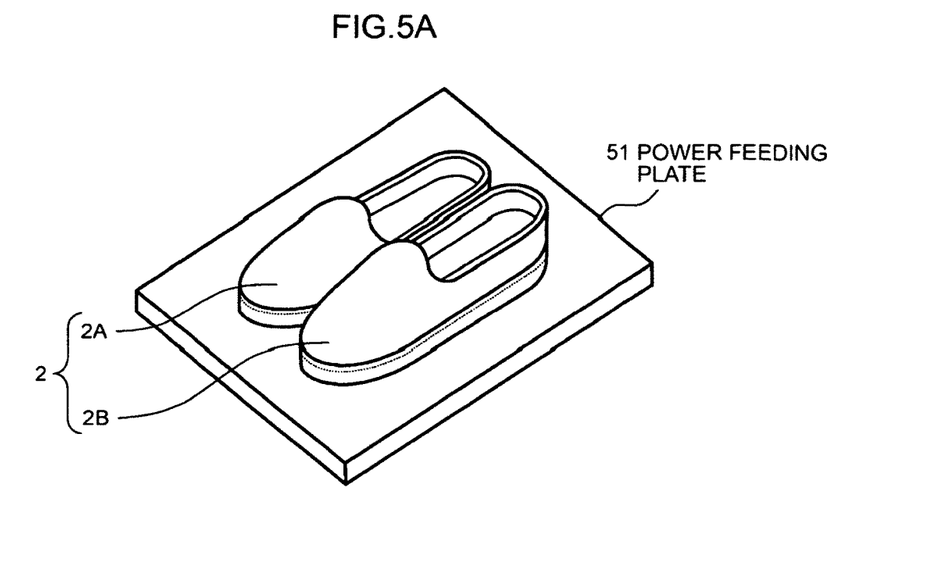
FIG. 5A is a perspective view explaining the wearable gait detection system according to another embodiment.
Figure 5B:
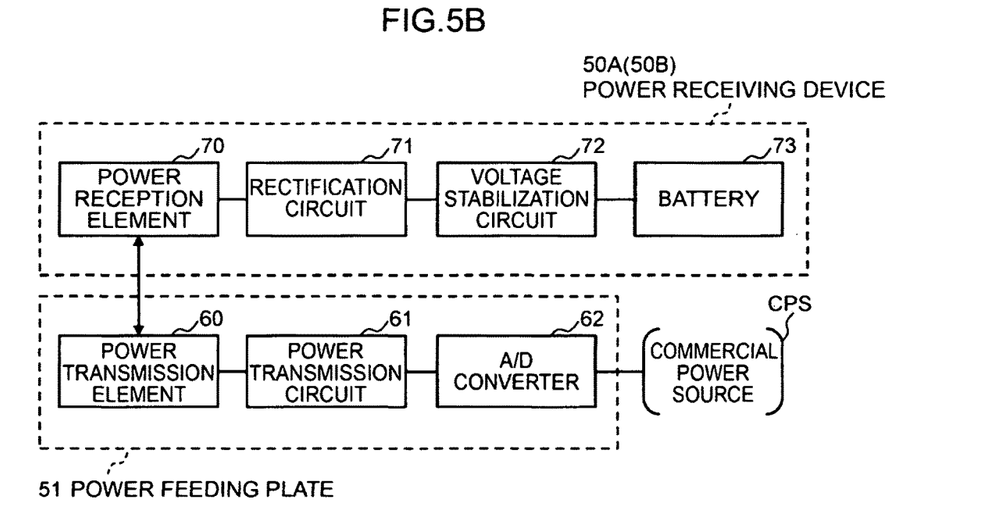
FIG. 5B is a block diagram explaining the wearable gait detection system according to another embodiment.

The power feeding system is configured, as shown in FIG. 5A and FIG. 5B, from a power receiving device 50A (50B) which is built into each shoe 2A (2B) of the wearable gait detection device 2, and a power feeding plate 51 which is mounted on each shoe 2A (2B) and which is capable of feeding power in a wireless manner.

The power feeding plate 51 has a flat plate shape capable of simultaneously mounting the pair of shoes 2A, 2B, and has a power transmission element 60, a power transmission circuit 61 and an A/D converter 62 built therein. The AD converter 62 converts the alternating current power (AC), which is supplied from a commercial power source CPS via an AC cable (not shown), into a direct current power (DC).

The power transmission circuit 61 generates high frequency power for wireless power transmission based on the direct current power supplied from the AD converter 62. The power transmission element 60 includes a power feeding coil as a power feeding device, and a resonance coil as a resonance device which resonates based on electromagnetic induction.

The power receiving device 50A (50B) includes a power reception element 70, a rectification circuit 71, a voltage stabilization circuit 72 and a battery (secondary battery) 73, and is built into the bottom part of each shoe 2A (2B). The power reception element 70 includes a power feeding coil as a power feeding device, and a resonance coil as a resonance device which resonates based on electromagnetic induction. When the self-resonant frequency of the resonance coil of the power transmission element 60 and the resonance coil of the power reception element 70 is a match, this will result in a relation of magnetic resonance coil, and power can be efficiently supplied.

The rectification circuit 71 rectifies the alternating current power received from the power reception element 70 and supplies it as a direct current (DC) power to the voltage stabilization circuit 72. The voltage stabilization circuit 72 converts the DC power supplied by the rectification circuit 71 into a predetermined DC voltage, and supplies the same to the battery 73 to charge the battery 73. The battery 73 supplies a drive power source of the overall device of the wearable gait detection device 2 under the control of the control part 20.

As described above, with the wearable gait detection device 2, by simply placing the pair of shoes 2A, 2B on the power feeding plate 51, the respective batteries 73 built into the shoes 2A, 2B can be automatically charged. By placing the power feeding plate 51 at the front porch or shoe box of the wearer's home, the wearer can recharge the shoes without any sense of discomfort during one's daily life.

REFERENCE SIGNS LIST

1 . . . walking ability improvement system, 2 . . . wearable gait detection device, 3 . . . information terminal device, 4 . . . management server, 10 . . . floor reaction sensor, 11 . . . optical position sensor, 12 . . . hexaxial motion sensor, 13 . . . sensory output part, 14 . . . control part, 20, 30 . . . control part, 21 . . . memory, 22, 31 . . . communication part, 40 . . . centroid position calculation part, 41 . . . foot movement locus calculation part, 42 . . . obstacle detection part, 43 . . . manifestation recognition part, 44 . . . sensory stimulation generation part, 50A, 50B . . . power receiving device, 51 . . . power feeding plate, 73 . . . battery.

The invention claimed is:

1. A wearable gait detection device which detects a gait in a state where a wearer is wearing a pair of left and right shoes, comprising:
   a floor reaction sensor which is mounted on an inner bottom part of each of the shoes and which measures a load of a sole of the wearer's feet;
   a motion sensor which is installed at a predetermined position of each of the shoes and which detects one or more of acceleration and angular velocity during movement of the feet;
   a micro-computer controller having a memory storing a data representing a stored centroid position of each of the feet, which:
      calculates a centroid position of each of the feet based on changes in each load measured by the floor reaction sensor;
      calculates a movement locus of each of the feet based on each of the one or more of acceleration and angular velocity detected by the motion sensor;
      recognizes manifestation in a brain according to a specificity of centroid fluctuation of each of the feet based on the calculated centroid position and movement locus of each of the feet,
      wherein the micro-computer controller recognizes the manifestation by comparing the calculated centroid position of each of the feet to the stored data representing a stored centroid position of each of the feet; and
   one or more of a light source, speaker, or vibration motor which feeds back a sensation to the wearer based on a recognition result of the manifestation recognized by the micro-computer controller.

2. The wearable gait detection device according to claim 1,
   wherein, in a case where the micro-computer controller has recognized a predetermined manifestation, the micro-computer controller sets a level and a transmission pattern of the sensation to be transmitted to the wearer by the one or more of a light source, speaker, or vibration motor according to a level of specificity of the centroid fluctuation of each of the feet.

3. The wearable gait detection device according to claim 1, further comprising:
   an optical position sensor which is mounted at a front end of each of the shoes and which detects an obstacle in front of the wearer's feet while the wearer is walking,
   wherein the micro-computer controller sends a specified warning signal which controls the one or more of a light source, speaker, or vibration motor to feed back the sensation to the wearer based on a detection result of the optical position sensor only when the micro-computer controller has recognized a predetermined manifestation.

4. A walking ability improvement system, comprising:
the wearable gait detection device according to claim 1;
a first data transceiver which is provided to the wearable gait detection device and which sends data representing the centroid fluctuation of each of the feet based on the manifestation recognized by the micro-computer controller;
a second data transceiver which is provided separately from the wearable gait detection device and which receives the data sent from the first data transceiver; and
a data terminal which sends the data received via the second data transceiver to a management server via a communication line.

5. The walking ability improvement system according to claim 4,
wherein the one or more of a light source, speaker, or vibration motor is provided to the pair of shoes and/or the data terminal device.

6. The walking ability improvement system according to claim 4,
wherein the micro-computer controller senses progression of manifestation in the wearer's brain based on the data read from the management server via the data terminal, and wherein the micro-computer controller sets the level and transmission pattern of the sensation to be transmitted to the wearer by the one or more of a light source, speaker, or vibration motor according to the progression of manifestation obtained from micro-computer controller.

7. A wearable gait detection system, comprising:
the wearable gait detection device according to claim 1; and
a power feeding system comprising
a power feeding plate which is provided separately from the wearable gait detection device and which is capable of feeding power, from a power source in a non-contact manner; and
a power charging circuit which is built into each of a pair of shoes of the wearable gait detection device, and which receives power fed from the power feeding plate, and feeds the received power to a rechargeable battery for feeding operating power to an overall circuit in each of the shoes.

* * * * *